United States Patent [19]
Vachss

[11] Patent Number: 5,313,072
[45] Date of Patent: May 17, 1994

[54] OPTICAL DETECTOR FOR WINDSHIELD WIPER CONTROL

[75] Inventor: Frederick Vachss, Thousand Oaks, Calif.

[73] Assignee: Rockwell International Corporation, Seal Beach, Calif.

[21] Appl. No.: 18,689

[22] Filed: Feb. 16, 1993

[51] Int. Cl.$^5$ .................................... G01N 15/06
[52] U.S. Cl. .................. 250/573; 250/227.25; 340/602
[58] Field of Search ............... 250/573, 222.2, 227.25; 340/583, 602; 318/444

[56] References Cited

U.S. PATENT DOCUMENTS

| | | | |
|---|---|---|---|
| 4,620,141 | 10/1986 | McCumber et al. | 318/483 |
| 4,956,591 | 9/1990 | Schierbeek et al. | 318/483 |
| 4,973,844 | 11/1990 | O'Farrell et al. | 250/341 |
| 5,059,877 | 10/1991 | Teder | 318/444 |
| 5,225,669 | 7/1993 | Hasch et al. | 250/214 A L |

*Primary Examiner*—Edward P. Westin
*Assistant Examiner*—T. Davenport
*Attorney, Agent, or Firm*—John C. McFarren

[57] ABSTRACT

An optical device is provided for detecting the degree of obscuring moisture or precipitation on the windshield of an automotive vehicle. A source of light, such as a light emitting diode (LED) or a laser diode, is positioned to illuminate the windshield. An optical imager and detector array senses light emitted by the source, either transmitted or reflected by the windshield, and imaged on the array. The light source and detector may be positioned in convenient, out-of-the-way locations inside or outside the windshield. When the windshield is free of obscuring precipitation, light from the source is imaged on a sensor of the array aligned with the optical axis of the imager. When obscuring moisture or precipitation is present on the windshield, light is scattered such that significant portions are imaged on sensors off the optical axis of the imager. The amount and spatial distribution of light received off the optical axis provides an indication of the degree of obscuration caused by light scattering moisture or precipitation present on the windshield. The detector is connected to the windshield wiper system of the vehicle to control activation of the wiper based on the optical detection of obscuring moisture or precipitation on the windshield.

9 Claims, 1 Drawing Sheet

OPTICAL DETECTOR FOR WINDSHIELD WIPER CONTROL

TECHNICAL FIELD

The present invention relates to windshield wiper systems for automotive vehicles and, in particular, to an optical detector for measuring windshield obscuration and adjusting the frequency and/or speed of a windshield wiper in response to changing rates of precipitation.

BACKGROUND OF THE INVENTION

Windshield wipers for modem automotive vehicles typically have several operating modes, such as fast, normal, and intermittent, that may be selected manually with a switch, dial, or sliding control. A driver generally activates the wiper system when the view through the windshield becomes distorted or obscured because of accumulated precipitation. The intermittent operating mode allows the driver to select a frequency of wiper operation that matches the intensity or rate of precipitation. When operated at the optimum speed and/or frequency, a windshield wiper provides good driver visibility without the distraction and annoyance of excessive activation.

When driving in conditions of variable precipitation, drivers often find themselves continually adjusting the speed and/or frequency of windshield wiper operation. Because each setting of the conventional wiper control provides a fixed speed and rate of activation, the setting must be manually adjusted every time the rate of precipitation changes. This increases driver workload (and annoyance) and diverts the driver's attention away from the task of driving the vehicle. What is needed, therefore, is a device for automatically controlling a windshield wiper to provide the optimum speed and/or frequency of operation in response to changing rates of precipitation. Such a device would provide an improvement in safety as well as driver convenience.

SUMMARY OF THE INVENTION

The present invention is an optical device for detecting and measuring the degree of obscuration caused by moisture or precipitation on a windshield of an automotive vehicle. The optical device comprises a point source of light, such as a light emitting diode (LED) or a laser diode, positioned to illuminate the windshield, and an optical imager having optics for imaging light emitted by the source onto a detector array. The light source and optical imager may be positioned in convenient, out-of-the-way locations inside or outside the windshield. Depending on its location, the optical imager is aligned to receive light from the source that is either transmitted or reflected by the windshield. When the windshield is free of obscuring matter such as precipitation, light from the source is imaged on a center element of the detector array that is aligned with the optical axis of the imager. When precipitation is present, however, the light is scattered and significant portions are imaged off the optical axis and detected by off-axis elements of the detector array. The amount of light received off the optical axis provides an indication of the degree of obscuration caused by light scattering moisture or precipitation present on the windshield. The detector array may include a readout multiplexer and microprocessor connected to the windshield wiper system of the vehicle for controlling activation of the wiper based on the optical detection of obscuring moisture or precipitation on the windshield.

A principal object of the invention is to provide a method and apparatus for optically measuring the degree of obscuration caused by moisture or precipitation on an automotive windshield. Features of the invention are a point source of light for illuminating the windshield and an optical imager having a sparse detector array for sensing light imaged both on and off the optical axis of the imager. An advantage of the invention is automatic activation of the windshield wiper system at the optimum speed and/or frequency in response to changing rates of precipitation.

BRIEF DESCRIPTION OF THE DRAWINGS

For a more complete understanding of the present invention and for further advantages thereof, the following Detailed Description of the Preferred Embodiments makes reference to the accompanying Drawings, in which.

DETAILED DESCRIPTION OF THE PREFERRED EMBODIMENTS

Figure 1:
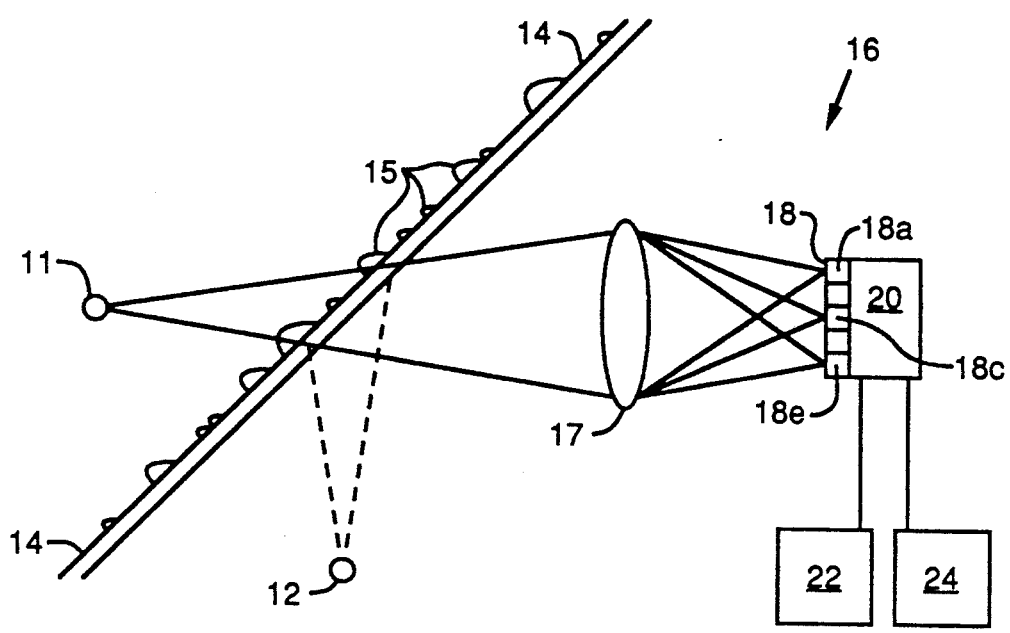
FIG. 1 is a schematic diagram illustrating an optical system of the present invention for detecting obscuring moisture or precipitation on a windshield of an automotive vehicle.

Alternative embodiments of the windshield obscuration detecting system of the present invention are illustrated schematically in FIG. 1. The optical system includes a small light source 11 or 12 for illuminating a windshield 14 of an automotive vehicle. An optical imaging apparatus 16 is positioned for sensing light emitted from source 11 or 12. In one embodiment light source 11 and optical imager 16 are located on opposite sides of windshield 14, whereas in an alternative embodiment light source 12 is located on the same side as optical imager 16. Light for source 11 is transmitted through windshield 14 to optical imager 16, whereas in the alternative embodiment light from source 12 is reflected by windshield 14 to optical imager 16.

The light source and imager of the present invention may be positioned in convenient, out-of-the-way locations inside or outside the vehicle and on the same or different sides of the windshield. For clarity of explanation, but not limitation, the following detailed description is directed to the embodiment comprising light source 11 outside the vehicle and optical imager 16 on the other side of windshield 14 inside the vehicle. Light source 11, which may comprise an LED, laser diode, or other small light source, may be located in the vicinity of a windshield washer spray nozzle, for example. Optical imager 16 may be mounted out of view of the driver behind a rearview mirror (i.e., between windshield 14 and the rearview mirror), for example. An embodiment, such as light source 12 and optical imager 16, having both emitter and imager mounted inside the vehicle may prove to be easier to maintain in alignment and free of interfering dirt and dust.

As illustrated schematically in FIG. 1, light from source 11 is imaged by a lens 17 onto an imaging plane 18 of a detector array comprising a plurality of individual sensing elements 18a–18e. Lens 17 may comprise a conventional optical lens, a Fresnel lens, or a system of lenses, for example. Sensors 18a–18e may comprise photodetectors or IR sensors as are well known in the sensor art. Imaging plane 18 of the detector may comprise a sparse one or two dimensional array of sensors, such as 18a–18e. Typically, sensor array 18a–18e is connected to a readout multiplexer and microprocessor 20 as is also well known in the art.

In the absence of precipitation or other light scattering obscurations on windshield 14, light from source 11 is imaged on the center of the detector array, which is aligned with the optical axis of imager 16 (i.e., on a small area directly behind the optical center of lens 17), as illustrated by the lines of focus merging on central sensor 18c. When obscuring moisture or precipitation 15, such as water droplets, snow flakes, sleet, etc., is present on windshield 14, light from source 11 (or from source 12 in the reflective embodiment) is scattered sufficiently for portions of the light to be imaged off the optical axis of imager 16, as illustrated by the lines of focus merging on sensors 18a and 18e. Thus, a small number of sensors 18a–18e placed on and at varying distances from the optical axis can determine the light intensity on image plane 18 as a function of the distance from the optical axis. The minimum number of individual sensors required for operation of the present invention is two, one on the optical axis and one off the optical axis. Additional sensors, such as sensors 18a–18e, provide more data for microprocessor 20 to perform sophisticated sensing and measuring functions. The relative intensities of the light imaged on-axis and off-axis at plane 18, and the distance of the imaged light from the optical axis, are functions of the type and amount of light obscuring (or distorting) moisture or precipitation 15 present on windshield 14. For example, condensation (or "fog") on the inside surface of windshield 14 would scatter light off the optical axis somewhat less than larger rain droplets 15 on the outside of windshield 14. Therefore, optical imager 16 would be able to discriminate between different types and amounts of light scattering moisture and precipitation on windshield 14.

The system of the present invention is distinctly different from systems that simply measure the amount of light scattered from windshield 14 without using an imaging system. Such direct scattering measurements would respond equally to many sources of stray or scattered light in addition to precipitation, even those that would not obscure visibility. Optical imager 16 of the present invention detects and measures the spatial distribution of scattered light, thus enabling a determination of the degree of windshield obscuration. The imaging system of the present invention provides a high signal-to-noise ratio by directly collecting light from source 11, more closely replicates the imaging process that occurs in the driver's vision, and is less prone to false detection than known alternative systems.

To further improve discrimination of light from source 11, source 11 and optical imager 16 may be designed to emit and detect a specific, narrow wavelength of radiation, which may also be pulsed at a known rate to separate and identify it from other sources. These variations in the basic imaging system of the present invention are believed to be well within the ability of one having ordinary skill in the art of optical emitters and detectors.

Microprocessor 20 of optical imager 16 may be connected, for example, to the vehicle's windshield wiper actuation system 22 and/or to a window defroster or defogger system 24, which may comprise a hot air blower or electrical heating grid, for example. In its most basic operating mode, the system of the present invention provides a signal to wiper system 22 to activate a sweep of the wipers upon detection of precipitation 15 at some threshold level of windshield obscuration. Thus, in an intermittent operating mode, optical imager 16 would either actuate a wiper sweep or not depending on the presence or absence of obscuring moisture or precipitation 15. This mode of operation would automatically adjust the wiper sweep rate (i.e., frequency of activation) to match changing rates of precipitation. Microprocessor 20 could include logic circuitry, as is well known, that would provide for varying the actual wiper speed as well as the frequency of activation. The threshold level of windshield obscuration for wiper activation could be preset, or it could be a value determined (and stored in temporary memory, for example) upon manual wiper activation by the driver. In addition, logic circuitry would be able to determine the presence of condensation or frost based on the spatial distribution of the scattered light detected at plane 18 and activate window defroster or defogger system 24 as necessary.

Although the present invention has been described with respect to specific embodiments thereof, various changes and modifications can be carried out by those skilled in the art without departing from the scope of the invention. Therefore, it is intended that the present invention encompass such changes and modifications as fall within the scope of the appended claims.

I claim:

1. A method of detecting obscuring moisture on a windshield of an automotive vehicle, comprising the steps of:
   illuminating the windshield with a source of light;
   imaging said source of light along an optical axis and onto an imaging plane;
   providing a light detector array having a plurality of light sensors on said imaging plane and centered on said optical axis for detecting said imaged source of light;
   detecting intensity of said light imaged on a central one of said light sensors located on said optical axis;
   detecting intensity of said light imaged on other ones of said light sensors located off said optical axis; and
   measuring the intensity of said detected off-axis light versus said detected on-axis light for determining the presence of obscuring moisture on said windshield.

2. The method of claim 1, further comprising the step of measuring distance of said detected off-axis light from said optical axis for determining the type and amount of obscuring moisture on said windshield.

3. The method of claim 2, further comprising the step of connecting a microprocessor to said detector array and to a windshield wiper actuation system, said microprocessor providing a signal for activating said wiper system upon detection of obscuring moisture on said windshield.

4. The method of claim 3, further comprising the step of automatically adjusting activation frequency and speed of said wiper system in response to said type and amount of obscuring moisture on said windshield.

5. The method of claim 3, further comprising the step of connecting said microprocessor to a window defogger system, said microprocessor providing a signal for activating said defogger system upon detection of said type and amount of obscuring moisture in the form of condensation on said windshield.

6. A method of detecting obscuring matter on a windshield of an automotive vehicle, comprising the steps of:
 illuminating the windshield with a point source of light;
 imaging said point source of light along an optical axis and onto an imaging plane;
 providing a light detector array having a plurality of light sensors on said imaging plane;
 aligning said light detector array with said optical axis for detecting said imaged point source of light;
 detecting intensity of said light imaged on one of said light sensors aligned with said optical axis;
 detecting intensity of said light imaged on other ones of said light sensors located off said optical axis;
 measuring the intensity of said detected off-axis light versus said detected on-axis light for determining the presence of obscuring matter on said windshield; and
 measuring the distance of said detected off-axis light from said optical axis for determining the type and amount of obscuring matter on said windshield.

7. The method of claim 6, further comprising the step of connecting a microprocessor to said detector array and to a windshield wiper actuation system, said microprocessor providing a signal for activating said wiper system upon detection of a threshold level of obscuring matter on said windshield.

8. The method of claim 7, further comprising the step of automatically adjusting activation frequency and speed of said wiper system in response to said type and amount of obscuring matter on said windshield.

9. The method of claim 8, further comprising the step of connecting said microprocessor to a window defogger system, said microprocessor providing a signal for activating said defogger system upon detection of said type and amount of obscuring matter in the form of moisture condensation on said windshield.

* * * * *